United States Patent [19]

Götze

[11] Patent Number: 4,476,724

[45] Date of Patent: Oct. 16, 1984

[54] AUDIOMETER

[75] Inventor: Gerd-Wolfgang Götze, Berlin, Fed. Rep. of Germany

[73] Assignee: Robert Bosch GmbH, Stuttgart, Fed. Rep. of Germany

[21] Appl. No.: 439,423

[22] Filed: Nov. 5, 1982

[30] Foreign Application Priority Data

Nov. 17, 1981 [DE] Fed. Rep. of Germany ....... 3145566

[51] Int. Cl.$^3$ .............................................. A61B 4/07
[52] U.S. Cl. ........................................ 73/585; 381/56
[58] Field of Search .......................... 381/56; 73/585; 340/784, 815.11, 753, 754; 179/107 FD, 107 R

[56] References Cited

U.S. PATENT DOCUMENTS 4,107,465  8/1978  Charlebois et al. .................... 73/585
4,109,106  8/1978  Voss ...................................... 73/585
4,250,503  2/1981  Shanks ................................. 340/754

OTHER PUBLICATIONS

"Arzt und Wirtschaft", pp. 44, 45, Sep. 1979.
Hearing Instruments, 1977 p. 41.

Primary Examiner—G. Z. Rubinson
Assistant Examiner—James L. Dwyer
Attorney, Agent, or Firm—Frishauf, Holtz, Goodman & Woodward

[57] ABSTRACT

An audiometer which can be battery operated, is reliable and economical in current consumption has a digital control unit (10) which controls a LCD in matric form (11, 26). The digital control unit, in its simplest form, includes a data input stage (12) having two inputs (16, 18) receiving, respectively, input signals representative of amplitude and tone, or a spoken word, and a further input (14) which is test-person controlled, to provide a perception signal, operated by the person to be tested when the level of a certain tone, generated by a tone generator (G, 21) is perceived, or a spoken word is correctly heard. The data input stage is connected to a data bus which provides the respective data to a driver circuit (24) to drive the LCD matrix. Various accessories can be provided, such a curve generating stage (45), a memory (42), an output unit for a recorder, such as a plotter, and a separate input/output state (46) to receive, for example, stored data for comparison of an audiogram being taken of a test-person with prior, or statistically derived audiograms.

19 Claims, 3 Drawing Figures

AUDIOMETER

The present invention relates to an audiometer and more particularly to an audiometer to test the perception level of sound of various frequencies by patients, or persons requiring hearing tests.

BACKGROUND

It has been previously proposed to provide audiometers in which the test frequency or test tones are controlled by sliders which are arranged at right angles with respect to each other. One of the sliders controls the frequency of the tone and the other slider controls the respective amplitude, or sound pressure level. Each pair of parameters—frequency and level—is indicated on the coordinate system, typically a Cartesian coordinate system by an illuminated dot. The abscissa represents frequency, and the ordinate the sound level. A diagramatic, or cross section paper can be placed on the indicator and the luminescent spots can be marked so that, at the end of a test, a complete audiogram is present. The luminescent dot is moved mechanically, or, in other words, a lightbulb which is illuminated each time at a test level and frequency is moved on the coordinate board. For precision in measurement, it is necessary that the coordinate or cross slide arrangement be, itself, a high precision structure.

A tone audiometer of this kind is described in the literature, see for example "Arzt und Wirtschaft", 1979, issue 9, pp 44 and 45. The apparatus there described is manufactured by the assignee of the present application.

It has also been proposed—see "Hearing Instruments", October 1977, p 41—that an oscilloscope be provided to indicate the respective coordinate points of the audiogram. The oscilloscope can be coupled to a plotter.

THE INVENTION

It is an object to provide an audiometer which is easily controlled and is substantially less expensive than previously known mechanical or oscillograph-type instruments.

Briefly, a generator is provided which can furnish signals at controlled frequencies at controlled amplitude levels, connected to a transducer, such as earphones, or one earphone, each, for an ear of a test person. When the test person perceives a certain tone of a predetermined frequency, a switch, a hearinafter "perception switch," is operated, indicating that, at the frequency, the then controlled or commanded tone level is necessary before the test person can perceive the tone. In accordance with the present invnetion, an electrical, digital matrix and matrix control circuit is provided, which receives the frequency control output signals and the amplitude control output signals applied to the generator and, upon sensing operation of the perception switch, provides a perception output signal; the matrix control circuit energizes a liquid crystal X-Y coordinate display matrix circuit to provide an output indication in coordinate form of the then pertaining amplitude of the then commanded frequency at the instant that the person being tested provides the perception output signal.

The audiometer has the advantage that the indicator is simple, reliable and requires only minimum electrical energy, so that it can be easily constructed in form of a portable instrument which is battery powered. If necessary and desirable, attachments can be provided which expand the utility of the system, for example by connecting the outputs to a curve generator which provides a luminuous trace between succeeding test points, so that a connected curve-type audiogram can be provided.

In accordance with a preferred embodiment, the audiometer utilizes a data bus which stores two succeeding pairs of measure values, that is, frequency and amplitude, to provide digital information derived therefrom and which then controls the two succeeding indicating elements of the liquid crystal display (LCD) matrix circuit to generate intermediate luminous dots so that an at least an approximately continuous curve will result. This provides an output which is particularly suitable for analysis. The stored data, in digital form, likewise can be used for transfer to long-time storage elements, such as magnetic tape or punch cards, for comparison with audiograms taken a later time.

DRAWING

Figures 1, 1A:
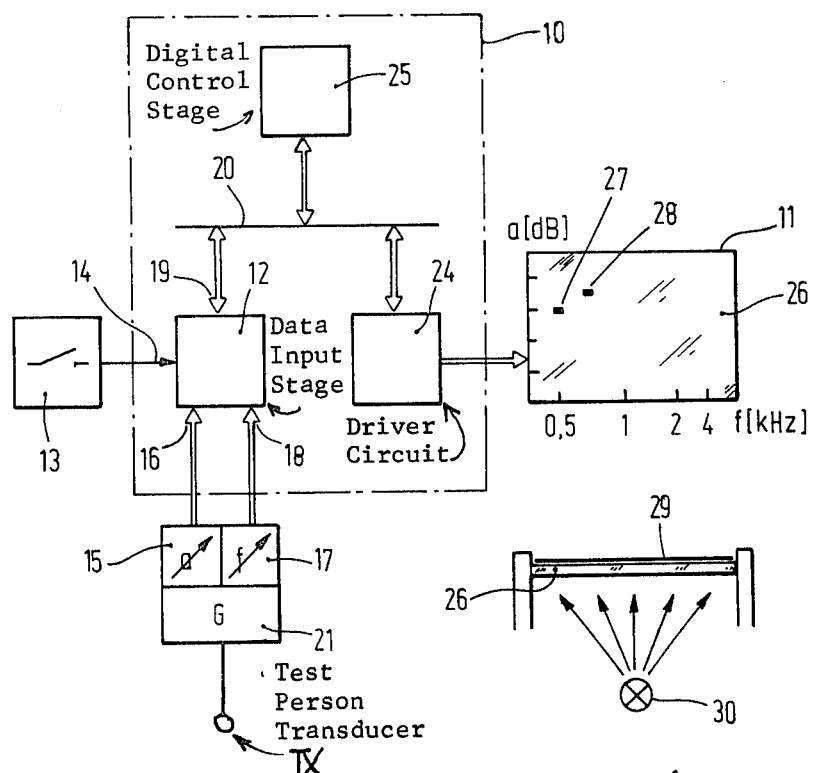
FIG. 1 is a schematic diagram of a control and indicating portion of an audiometer.
FIG. 1a is a schematic side view of the display portion of the audiometer of FIG. 1.

The audiometer of FIG. 1 includes a digital control unit 10 and a display unit 11. The digital control unit 10 has a data input stage 12, which has three inputs 14, 16, 18. Input 14 is connected to a test switch 13 which forms the perception switch, to be operated by the person being tested upon perceiving a tone. A tone frequency generator 21 is connected to a transducer TX, such as a single-ear earphone, transducer plug, dual earphones or the like, in accordance with the testing mode to be carried out. The generator 21 likewise is connected to a level or amplitude (a) controller 15 which is connected to input 16 of data input stage 12, and a frequency (f) controller 17 which is connected to the data input 18. The level, or amplitude controller 15 and the frequency controller 17 are, in one example, manually operated, for example by a testing operator. The data input stage 18 is connected via an input/output bus 19 with a data bus 20.

The level or amplitude controller 15 and the frequency controller 17 can be part of the frequency generator 21, which can be constructed in form of a well-known unit, providing signals at the frequencies required for an audiogram, for example from between 0 to 5 kHz, or higher, in dependence on the test to be carried out.

The data bus 20 is connected to a driver circuit 24, which has its output connected to the digital display 11. The data bus 20 is, further connected to a digital control stage 25. The display 11 x-y LCD matrix 26. The LCD matrix 26 may include the necessary decoding and matrix circuitry to provide indication by matrix elements 27, 28, located at respective x-axis and y-axis coordinates, representative, respectively, of frequency and amplitude. In LCD matrix units, the indicated elements appear in the form of dark or black points on a light background. FIG. 1a indicates, in schemcatic side view, the LCD display 11 with a graph paper 29 thereon to which the indicated coordinate levels can be transferred, for example manually with a pencil, or automatically, such as photographically. A light source 30 is located below the LCD element which provides uniform illumination over the entire plane of the LCD matrix, so that the dark points can be clearly distinguished.

Operation

Let it be assumed that the test operator sets a frequency of, for example, 500 Hz with frequency controller 17. The amplitude controller 15 is then operated to increase the tone pressure level slowly until the tested person, who, of course, will wear the transducer TX, just perceives the tone. At that point, the tested person will operate the perception switch 13. The digital control stage 25 will decode frequency and level as controlled by the controllers 17 and 15 to provide corresponding digital values to the data bus 20, which are applied to the driver circuit 24 to energize the LCD element 26 so that the appropriate indicating point 27 will be rendered dark or non-transparent. The position of the indicated element 27 can then be transferred, manually or automatically, e.g. photographically, to a cross section or diagram paper 29.

The test operator will then change the frequency of the output from generator 21 to another frequency, for example to 750 Hz. The level, or amplitude of the output signal, as heard in the transducer TX is then increased, in the same manner, until the tested person perceives the tone at the higher frequency and, when so perceived, provides an output via the perception switch 13 which, after being decoded and transformed into digital coordinate form, provides the output indication 28, which associates level, in db with the then commanded or controlled frequency. This indicated point likewise is transferred to the diagram sheet 29 and marked. Subsequent tests at different frequencies can be carried out and, at the termination of the test, a diagram with a complete audiogram is provided in which the perception levels at various frequencies are clearly apparent.

Figure 2:
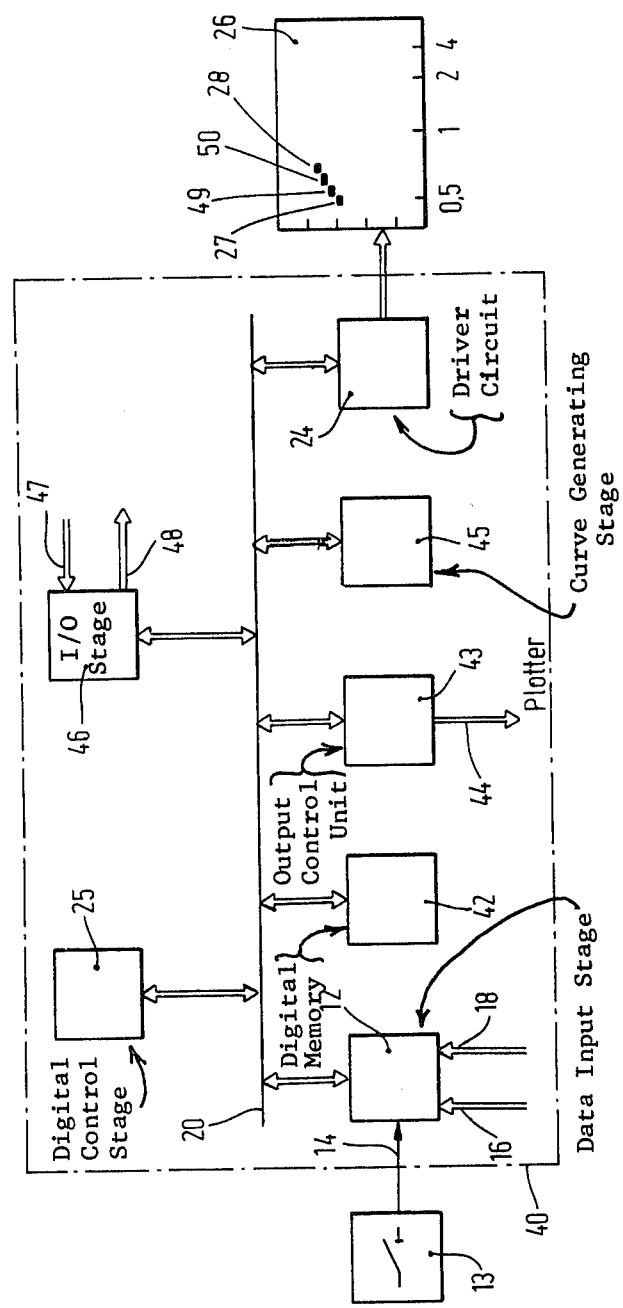
FIG. 2 is a block circuit diagram of the control and indicating portion of the audiometer illustrating components which can be used by way of attachment or expansion of the basic audiometer of FIG. 1.

Embodiment of FIG. 2

Basically, this embodiment is similar to that of FIG. 1 and similar elements have been given the same reference numerals and will not be explained again. The generator G, 21, and the control units 15, 17 have been omitted for clarity.

The tone audiometer 40 of FIG. 2 is amplified with respect to the tone audiometer 10 of FIG. 1 by the following elements: a digital memory 42, an output control unit 43 which has an output 44 which can be connected, for example, to external apparatus if available, for example a plotter, an input/output (I/O) stage 46 and a curve generating stage 45. Stages 42, 43, 45, 46 are connected to the data bus 20, as are stages 12, 24, 25. The I/O stage has an input 47 and an output 48. Function of stages, and operation: Let it be assumed that a test is to be carried out similar to the one described in connection with FIG. 1. The test generator G, by frequency controller 17 is set to a first audible frequency, and the audio pressure level is increased until the test person recognizes or perceives the frequency and operates switch 13. The digital control stage 25, which, preferably, is a microprocesser, then controls the following operations, in accordance with well-known and standard programming procedure: the pair of signal data—frequency and amplitude—are stored in the memory 42; they are connected to the output 44 from the output control unit 43, for example to control a plotter, if connected thereto; additionally, the data are applied to the curve generating stage 45, where they are also stored. Further, they are connected to the driver circuit 24. They are transferred from the driver circuit 24, suitably amplified, to the LCD matrix 26.

The next tone frequency is then commanded and the amplitude level changed until the test person perceived the tone and operates the perception switch 13. Changeover to a different frequency, and change of the level of the signal thereof, for example starting from a low level can be commanded automatically, in accordance with well-known sequencing steps stored in the digital control stage 25 and automatically controlling first switchover to a different frequency and then gradual increase in the output level from the generator 21. No test operator, then, is necessary. It is only necessary that the person to be tested must operate the perception switch each time when a new tone frequency is perceived. When the tone frequency has been perceived, and the perception switch operated, the associated pair of measured values are stored in the memory 42 and in the curve generating stage 45 at respective addresses. The curve generating stage 45, which can be a well-known and standard unit, forms a series of connecting values between the first stored measurement pairs and the second stored measurement pair, in a straight line, in the x-y coordinate system, and supplies this intervening information to the driver circuit 24 to so control the LCD display 26 that two sequential test points 27, 28 will have one or more indicating elements such as 49, 50 energized to be visible. An at least approximately continuous curve will then result, the continuity of the curve being determined by the fineness of subdivision of the LCD matrix.

The I/O stage is provided to furnish further outputs, for example to a computer which can calculate, or associate the outputs from a specific person to be tested with other information, such as, for example, statistically derived information to provide outputs over a population sample; and supply inputs which, for example, can be supplied to the LCD stage 26 before or after testing derived from a previously stored audiogram for comparison of a newly made audiogram with prior perception data from the same person or with reference, for example a statistical average to determine deviation of hearing perception by the particular person being tested from the input over terminal 47 derived, for example, from statistical values.

The memory 42 can be so arranged that its stores the measured values of a plurality of audiograms, at respective addresses associated, for example, with specific frequencies and specific test persons or testing events. The memory 42 stores a plurality of audiograms, for example by the same person, so that upon subsequent testing of a person, the results of a previous audiogram can be displayed on the LCD stage 26 so that the then generated audiogram can be directly compared with the previous one. Any possible improvement, or degradation of the hearing capability of the test person can thus be readily determined.

The various additional elements 42, 44, 45, 46 of FIG. 2 may be used together, or selectively, as special attachments or accessories with the basic audiometer 10 of FIG. 1, and provided either separately or selectively connectable as desired. Any selected combination can be provided.

The invention can be equally applied to a audiometer operating on the basis of the spoken word, to illustrate audiograms based on speech. If so arranged, the test person receives a group of words which are entered over input 18, for example from a recording, a tape, or the like. The level of reproduction in the transducer TX is preset, and the test person must repeat the words. Each word which is correctly reproduced is indicated by operation of the perception switch, functioning as a registering switch or button. At the end of a sequence of words, the audiometer will then provide an output representative of the percentage of the correctly recognized words and indicates the value of the respective associated sound pressure level. The abscissa, then, will not indicate the frequency in, for example, kHz, but, rather, a specific word, the ordinate, again, indicating the level. In a second sequence, the same series of words can be provided, for example at a higher level. The output indications of correctly recognized words of one series at one pressure level can then be compared, by storing the output indications after the first series, with the outputs in the second, and subsequent series at a higher auditory level.

Various changes and modifications may be made within the scope of the inventive concept, and features described in connection with one of the embodiments may be used with the other, within the scope of the inventive concept. Of course, the auditory material provided to the test person need not be pure tones of predetermined frequencies, or specific spoken words. Tones, music, single, or mixed frequencies may be used and will be referred to, hereinafter, as "test sounds", the natures of which—for example speech, music—or the frequency of which—for example as pure tones or tones with harmonics—can be suitably controlled. The frequency generator G, thus, can be supplemented by a microphone, or standard input device such as a series of works spoken in standard pronounciation and form and recorded on a tape and supplied, sequentially, with controlled amplitude by the amplitude control element 15. The respective standard words, or series of words then corresponds to the test sounds controlled by the controller 17 which, with control generator 21, merely controls frequency.

Suitable units for the respective stages are:
generator 21: 3×741 (MOTOROLA)
data input stage 12: MC 6850 (MOTOROLA)
digital control stage 25: 46-2716 (HITACHI)
digital memory 42: 46-2732 (HITACHI)
output control unit 43: MC 6850 (MOTOROLA)
driver circuit 24: 7216 (INTERSIL)
I/O stage 46: MC 6850 (MOTOROLA)
LCD matrix 26: customer designed matrix

I claim:

1. Audiometer to obtain test sounds, or frequency, versus perceived amplitude in diagrammatic x-y coordinate output form for testing hearing of a person for tones, music and speech having
an output unit (11) in form of a coordinate system in which amplitude forms one coordinate parameter and sound, or frequency another coordinate parameter;
means (21) for generating electrical test signals representative of test sounds or tones;
amplitude control means (15, 16) connected to said test sound or tone generating means for controlling the amplitude of the output thereof and providing an amplitude control output signal;
tone control means (17, 18) connected to said test sound or tone generating means for controlling the nature of the test sound or frequency of the test tone thereof, and providing a test sound control output signal;
test person transducer means (TX) transducing the test sound, or tone signals of the nature of the sound or at the frequency of the test tone and the level controlled by the tone control means and the amplitude control means, respectively;
and test person controlled response means (13, 14) providing an electrical perception output signal if a predetermined test sound, or tone has been perceived, comprising, in accordance with the invention,
an electronic digital matrix control circuit (10) receiving said amplitude control output signal, said test sound or tone control output signal and the perception output signal;
and wherein the output unit comprises a liquid crystal display (LCD) in matrix form (11, 26) connected to and controlled by said digital matrix control circuit and providing an output in x-y coordinate form of perceived amplitude of a respective test sound or frequency at the instant of reception of the perception output signal.

2. Audiometer according to claim 1 wherein the LCD comprises a plane LCD matrix (26) and a light illuminating source (30) located beneath the LCD matrix.

3. Audiometer according to claim 1 wherein the digital matrix control circuit (10, 40) includes a data bus (20);
and wherein a digital control unit (25) is provided, connected to the data bus.

4. Audiometer according to claim 3 further including a matrix driver circuit (24) connected to the data bus and to the LCD in matrix form (11, 26).

5. Audiometer according to claim 1 wherein said means for generating electrical signals comprises a tone or frequency generator means (21, G);
and said means (15, 16) for controlling the nature of the test sounds comprises frequency control means, controlling the output frequency of the tone generator.

6. Audiometer according to claim 1 wherein the means (21) for generating electrical signals comprises means (21) generating said signals in a form representative of spoken, or recorded test sounds;
and said means (15, 16) for controlling the nature of the test sounds comprises signal generator means associating a predetermined test sound, or spoken word with a characteristic output signal.

7. Audiometer according to claim 5 further including a data bus (20) connected to said means (21) for generating the electrical signals;
a driver circuit (24) connected to the data bus and providing driving power to the LCD in matrix form (11,26);
and wherein a data input stage (12) is provided, connected to said data bus and receiving the amplitude control output signal, the test control output signal and the perception output signal, and connecting, respectively, said signals to the driver circuit to energize the LCD in matric form in accordance with said signals.

8. Audiometer according to claim 7 further including an output control unit (43) connected to said data bus and providing output signals for an external recording apparatus.

9. Audiometer according to claim 7, for use with succeeding tests in which different test sounds or frequencies are supplied to the test person by the test person transducer means (TX), further including a curve generating stage (45) connected to said data bus and providing output signals to the driver stage (24) to generate, on said LCD in matrix form (11, 26) a straight line pattern between coordinate displays representative of the coordinates of amplitude and frequency of the test signals upon each succeeding reception of perception output signals.

10. Audiometer according to claim 5 further including an input/output stage (46) connected to the data bus to provide output signals representative of the signals supplied to the driver stage and to receive signals presentative of coordinate positions on the LCD in matrix form derived from an external input unit.

11. Audiometer according to claim 5 further including a digital memory (42) connected to said data bus to store the value of respective amplitude control output signals and test sounds control output signals, in pairs, upon, respectively, receiving a perception output signal associating said amplitude and test sound output signals.

12. Audiometer according to claim 6 further including a data bus (20) connected to said means (21) for generating the electrical signals;
a driver circuit (24) connected to the data bus and providing driving power to the LCD in matrix form (11,26);
and wherein a data input stage (12) is provided, connected to said data bus and receiving the amplitude control output signal, the test control output signal and the perception output signal, and connecting, respectively, said signals to the driver circuit to energize the LCD in matrix form in accordance with said signals.

13. Audiometer according to claim 6 further including an output control unit (43) connected to said data bus and providing output signals for an external recording apparatus.

14. Audiometer according to claim 13, for use with succeeding tests in which different test sounds or frequencies are supplied to the test person by the test person transducer means (TX), further including a curve generating stage (45) connected to said data bus and providing output signals to the driver stage (24) to generate, on said LCD in matrix form (11, 26) a straight line pattern between coordinate displays representative of the coordinates of amplitude and frequency of the test signals upon each succeeding reception of perception output signals.

15. Audiometer according to claim 6 further including an input/output stage (46) connected to the data bus to provide output signals representative of the signals supplied to the driver stage and to receive signals presentative of coordinate positions on the LCD in matrix form derived from an external input (47).

16. Audiometer according to claim 6 further including a digital memory (42) connected to said data bus to store the value of respective amplitude control output signals and test sounds control output signals, in pairs, upon, respectively, receiving a perception output signal associating said amplitude and test sound output signals.

17. Audiometer to obtain test sounds, or frequency, versus preceived amplitude in x-y coordinate diagrammatic output form for testing hearing of a test person for tones, music, and speech having
an output unit (11) in form of a coordinate system in which amplitude forms one coordinate parameter and sound, or frequency another coordinate parameter;
means (21) for generating electrical test signals representative of test sounds or tones, for use with succeeding tests, in which different test sounds or frequencies are supplied to the test person by a test person transducer means (TX);
amplitude control means (15, 16) connected to said test sound or tone generating means for controlling the amplitude of the output thereof and providing an amplitude control output signal;
tone control means (17, 18) connected to said test sound or tone generating means for controlling the nature of the test sound or frequency of the test tone thereof, and providing a test sound control output signal;
test person transducer means (TX) transducing the test sound, or tone signals of the nature of the sound or at the frequency of the test tone and the level controlled by the tone control means and the amplitude control means, respectively;
and test person controlled response means (13, 14) providing an electrical perception output signal if a predetermined test sound, or tone has been perceived,
comprising
an electronic digital matrix control circuit (10) receiving said amplitude control output signal, said test sound or tone control output signal and the perception output signal;
wherein the output unit comprises
a liquid crystal display (LCD) in x-y coordinate matrix form (11, 26) connected to and controlled by said digital matrix control circuit and providing an output in coordinate form of perceived amplitude of a respective test sound or frequency at the instant of reception of the perception output signal;
said audiometer further including a curve generating stage (45) connected to said data bus and providing output signals to the driver stage (24) to generate, on said LCD in matrix form (11, 26) a straight line pattern between coordinate displays representative of the coordinates of amplitude and frequency of the test signals upon each succeeding reception of perception output signals.

18. Audiometer according to claim 17, wherein said means for generating electrical signals comprises a tone or frequency generator means (21, G);
and said means (15, 16) for controlling the nature of the test sounds comprises frequency control means controlling the output frequency of the tone generator.

19. Audiometer according to claim 17, wherein the means (21) for generating electrical signals comprises means (21) generating said signals in a form representative of spoken, or recorded test sounds;
and said means (15, 16) for controlling the nature of the test sounds comprises signal generator means associating a predetermined test sound, or spoken word with a characteristic output signal.

* * * * *